United States Patent
Tieu et al.

(10) Patent No.: US 11,134,954 B1
(45) Date of Patent: Oct. 5, 2021

(54) BRAIDED EMBOLIZATION APPARATUS

(71) Applicant: AccuMedical Beijing Ltd., Beijing (CN)

(72) Inventors: Tai D. Tieu, Fountain Valley, CA (US); Jonathan D. Perez, Irvine, CA (US)

(73) Assignee: ACCUMEDICAL BEIJING LTD.

( * ) Notice: Subject to any disclaimer, the term of this patent is extended or adjusted under 35 U.S.C. 154(b) by 0 days.

(21) Appl. No.: 17/164,497

(22) Filed: Feb. 1, 2021

(51) Int. Cl.
    *A61B 17/12* (2006.01)
    *A61B 90/00* (2016.01)

(52) U.S. Cl.
    CPC .... *A61B 17/12145* (2013.01); *A61B 17/1215* (2013.01); *A61B 17/12113* (2013.01); *A61B 90/39* (2016.02); *A61B 2017/1205* (2013.01); *A61B 2090/3966* (2016.02)

(58) Field of Classification Search
    CPC .......... A61B 17/12145; A61B 17/1215; A61B 17/1214; A61B 17/12113; A61B 17/12122; A61B 2017/12054; A61B 2017/1205
See application file for complete search history.

(56) References Cited

U.S. PATENT DOCUMENTS

| | | | |
|---|---|---|---|
| 8,043,321 B2 | 10/2011 | Elliot | |
| 9,867,725 B2 | 1/2018 | Tieu et al. | |
| 10,206,796 B2 | 2/2019 | Tehrani et al. | |
| 10,624,771 B2 | 4/2020 | Lu | |
| 10,821,010 B2 | 11/2020 | Tehrani et al. | |
| 2018/0206849 A1* | 7/2018 | Hewitt | A61B 17/12186 |
| 2020/0138422 A1* | 5/2020 | Hebert | A61B 17/12154 |

* cited by examiner

*Primary Examiner* — Wade Miles
(74) *Attorney, Agent, or Firm* — Entralta P.C.; Justin G. Sanders; Peter D. Weinstein

(57) ABSTRACT

A braided embolization apparatus is disclosed. In at least one embodiment, a plurality of individual strands are braided together as an embolic braid having a proximal end and an opposing distal end, the embolic braid forming an elongated primary shape capable of being inserted into a catheter. During use of the apparatus, upon the distal end of the embolic braid subsequently exiting the catheter, the embolic braid is configured for moving into a shape memorized secondary shape capable of filling a target area of a patient's vascular system.

18 Claims, 4 Drawing Sheets

BRAIDED EMBOLIZATION APPARATUS

RELATED APPLICATIONS

Not applicable.

BACKGROUND

The subject of this patent application relates generally to neurovascular embolization devices, and more particularly to a braided embolization apparatus configured for providing improved stretch resistance, maximized surface area, increased radiopacity and improved shape retention, thereby resulting in a more effective treatment of cerebral aneurysms and cerebral arteriovenous malformations.

Applicant(s) hereby incorporate herein by reference any and all patents and published patent applications cited or referred to in this application.

By way of background, embolic coils are one example of devices that may be used to block blood flow into an aneurysm. Introducing one or more embolic coils into the affected vessel to slow the flow of blood allows the natural clotting process to form a more complete blockage. Embolic coils are typically made from bio-compatible materials, such as platinum, to minimize problems associated with tissue irritation and rejection. These coils are often shaped as complex three-dimensional curves that fill in portions of a blood vessel's lumen and slow blood flow therethrough. Often, polymeric fibers are added to the metallic coils to enhance the coil's thrombogenicity (i.e., its ability to cause the formation of clots).

In the treatment for an aneurysm, an embolic coil is inserted in the affected blood vessel using a catheter which has been introduced into the patient's vascular system, and is placed within the bulging, weakened section of the blood vessel. When in place, the coil expands to its operational size and shape, and slows down the flow of blood through the weakened section. Over time, a clot forms around the embolic coil, and blood flow through the weakened section is completely blocked. Thus, failure of this weakened section is less likely and the resulting hemorrhage may be prevented. A distal portion of the embolic coil may include radiopaque markers to facilitate positioning of the coil at the desired location within the blood vessel (e.g., adjacent to the weakened or damaged portion thereof). All or part of the coil may be flexible, so that it may follow the curvature of the catheter leading to the region of the vascular system to be treated.

Traditional embolic coils are formed using two major steps: 1) a wire of platinum or other bio-compatible material is wound into a helical spring, forming what is commonly referred to as a primary coil having a "primary shape;" and 2) the primary coil is in turn wound around a mandrel having a more complex shape and is subject to high heat to yield a secondary coil. The secondary coil thus is a coiled wire of complex shape, hereinafter referred to as the "secondary shape." In most cases, the recommended packing density of an aneurysm is 20-30% or more of the aneurysm's volume, which typically requires the deployment of multiple embolic coils. However, higher volumes may be difficult to achieve due to the delicate nature of aneurysms. Thus, there remains a need for embolization devices having relatively greater surface areas and improved shape retention.

Relatedly, many traditional embolic coils can suffer from unintended unraveling of the primary coil winding, on withdrawal or retrieval of the coil. This unraveling of the proximal part of the coil can occur when the distal part becomes stuck inside the mesh of previously inserted coils. An unraveled coil cannot be repositioned, and further withdrawal either leads to the removal of the remaining part of the coil or to coil fracture, resulting in thrombogenic coil material left in normal cerebropetal vessels. To try and correct this issue, some embolic coils now include a filament positioned centrally in the primary winding of the coil, such that the force of withdrawal is transmitted by the inner filament and not by the wound coil wire itself. Such filaments are typically made of nitinol, polyglycolic acid, or polypropylene and are attached to the proximal and distal ends of the coil. However, it has been suggested from clinical and experimental studies that the use of such filaments have a negative influence on the physical properties of the coil, such as coil softness, shape memory, and flexibility. Thus, there remains a need for embolic devices having improved stretch resistance without sacrificing coil softness, shape memory, or flexibility.

Aspects of the present invention fulfill these needs and provide further related advantages as described in the following summary.

It should be noted that the above background description includes information that may be useful in understanding aspects of the present invention. It is not an admission that any of the information provided herein is prior art or relevant to the presently claimed invention, or that any publication specifically or implicitly referenced is prior art.

SUMMARY

Aspects of the present invention teach certain benefits in construction and use which give rise to the exemplary advantages described below.

The present invention solves the problems described above by providing a braided embolization apparatus configured for providing improved stretch resistance, maximized surface area, increased radiopacity and improved shape retention, thereby resulting in a more effective treatment of cerebral aneurysms and cerebral arteriovenous malformations. In at least one embodiment, a plurality of individual strands are braided together as an embolic braid having a proximal end and an opposing distal end, the embolic braid forming an elongated primary shape capable of being inserted into a catheter. During use of the apparatus, upon the distal end of the embolic braid subsequently exiting the catheter, the embolic braid is configured to move into a shape memorized secondary shape capable of filling a target area of the patient's vascular system.

Other features and advantages of aspects of the present invention will become apparent from the following more detailed description, taken in conjunction with the accompanying drawings, which illustrate, by way of example, the principles of aspects of the invention.

BRIEF DESCRIPTION OF THE DRAWINGS

The accompanying drawings illustrate aspects of the present invention. In such drawings.

The above described drawing figures illustrate aspects of the invention in at least one of its exemplary embodiments, which are further defined in detail in the following description. Features, elements, and aspects of the invention that are referenced by the same numerals in different figures represent the same, equivalent, or similar features, elements, or aspects, in accordance with one or more embodiments.

DETAILED DESCRIPTION

Figure 1:
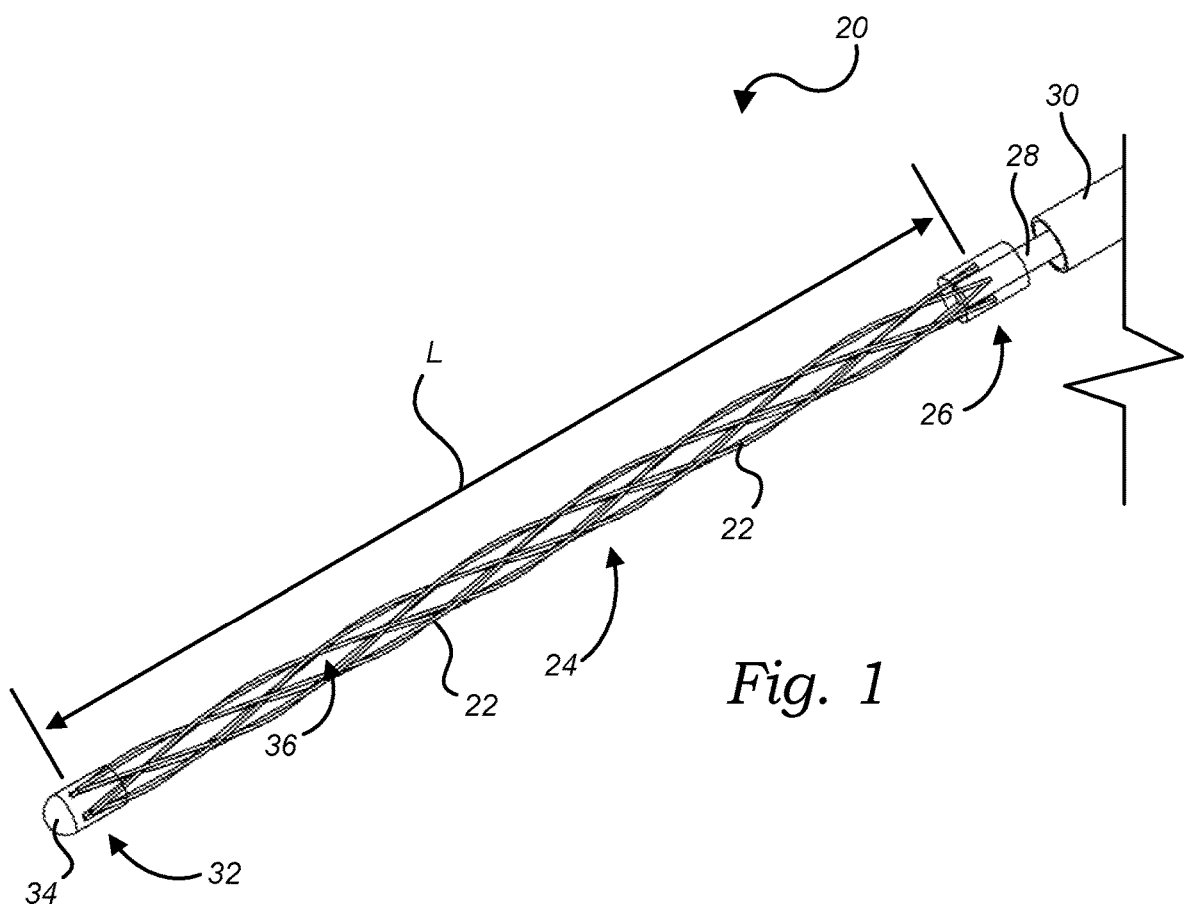
FIG. 1 is a partial perspective view of an exemplary braided embolization apparatus, in accordance with at least one embodiment.

Turning now to FIG. 1, there is shown a partial perspective view of an exemplary braided embolization apparatus 20. In at least one embodiment, the apparatus 20 comprises a plurality of individual strands 22 braided together to form an embolic braid 24 having an elongated primary shape. At the outset, it should be noted that the term "strand" is intended in its broadest meaning to include a wire, a fiber, a filament, or other single elongated member. Additionally, the term "radiopaque" is utilized for its normal meaning of being radiodense, that is, formed of one or more materials (such as platinum, chromium, cobalt, tantalum, tungsten, nitinol, gold, silver, stainless steel or alloys thereof, for example) which inhibit the passage of electromagnetic radiation to increase visibility during imaging. With continued reference to FIG. 1, a proximal end 26 of the embolic braid 24 is removably engageable with a delivery mechanism 28, such as a wire for example, for moving the embolic braid 24 through a catheter 30. In that regard, it should be noted that the delivery mechanism 24 and catheter 30 depicted in FIG. 1 are merely exemplary and shown for illustrative purposes. In further embodiments, the apparatus 20 may utilize any type of delivery mechanism and/or catheter—now known or later developed—capable of allowing the apparatus 20 to substantially carry out the functionality described herein. In at least one embodiment, an opposing distal end 32 of the embolic braid 24 provides an end cap 34 for maintaining the braided arrangement of the strands 22. In at least one such embodiment, the end cap 34 is constructed out of one or more radiopaque materials to facilitate positioning of the embolic braid 24 at a desired location within a blood vessel or another target area within a vascular system of a patient. In at least one alternate embodiment, one or both of the proximal and distal ends 26 and 32 are simply closed, sealed or otherwise finished so as to maintain the braided arrangement of the strands 22.

In at least one embodiment, given that the embolic braid 24 is comprised of a plurality of strands 22 braided together, the properties of the embolic braid 24 may be selectively tailored to fit the requirements of the medical procedure for which the apparatus 20 is to be used. For example, in at least one embodiment, one or more individual strands 22 may be comprised of materials that are different from the other strands 22 of the embolic braid 24. In at least one such embodiment, at least one of the strands 22 is comprised of one or more radiopaque materials, while the remaining strands 22 are comprised of one or more non-radiopaque materials (such as fiber, plastic, polymers, multi-layer composites or other biocompatible materials, for example). In this way, the radiopacity of the embolic braid 24 may be selectively tailored (by including a lower or higher quantity of radiopaque strands 22) while also maintaining the requisite structural integrity for necessary shape retention, as discussed further below. In at least one further embodiment, one or more individual strands 22 may be comprised of both radiopaque and non-radiopaque materials. Those skilled in the art will understand that other suitably bio-compatible materials may be used so long as they possess appropriate mechanical properties. Additionally, in at least one embodiment, one or more individual strands 22 has a strand diameter D1 (i.e., an outer diameter) that is different than a strand diameter D1 of the remaining strands 22 of the embolic braid 24, which allows a primary diameter D2 of the embolic braid 24 (i.e., an outer diameter of the embolic braid 24 while in the primary shape) to be selectively tailored which, in turn, can alter the mechanical performance of the embolic braid 24. In at least one embodiment, the primary diameter D2 is also dependent on the quantity of strands 22 as well as the braiding pattern utilized by the embolic braid 24, as discussed further below. The relative rigidity or softness of the embolic braid 24 may also be selectively tailored based on one or more of the quantity of strands 22, the strand diameter D1 of each strand 22, the material(s) of construction of each strand 22, and the braiding pattern utilized by the embolic braid 24. In at least one embodiment, one or more individual strands 22 may be constructed out of, impregnated or coated with an at least one drug or drug releasing agent (hereinafter generally referred to as a "therapeutic" for simplicity purposes), such that the at least one therapeutic is capable of being automatically released into the patient's bloodstream when the apparatus 20 is deployed within the patient's vascular system. In at least one such embodiment, one or more strands 22 are coated with a therapeutic that promotes thrombosis.

Figure 2:
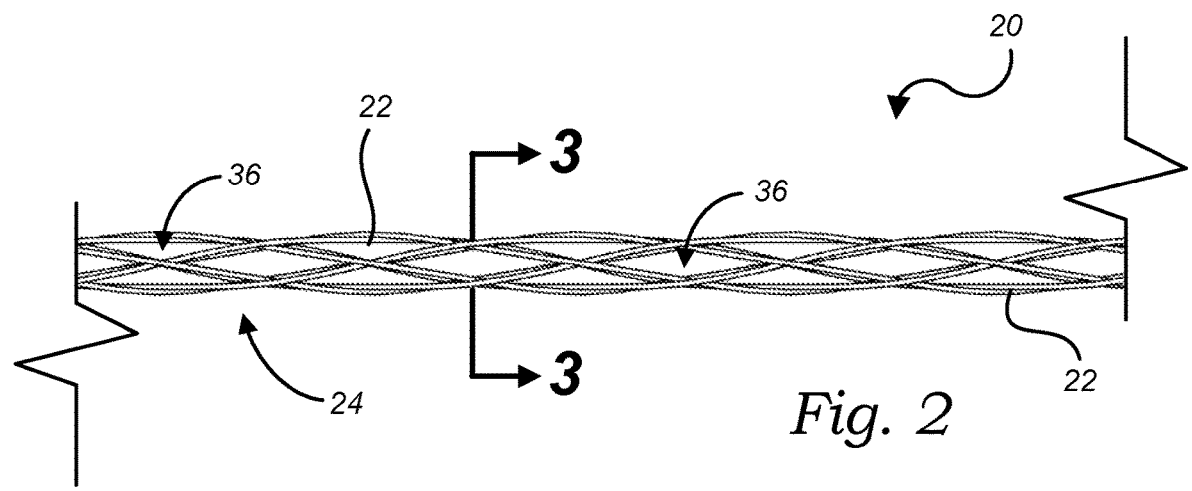
FIG. 2 is a partial side view thereof, in accordance with at least one embodiment.
Figure 3:
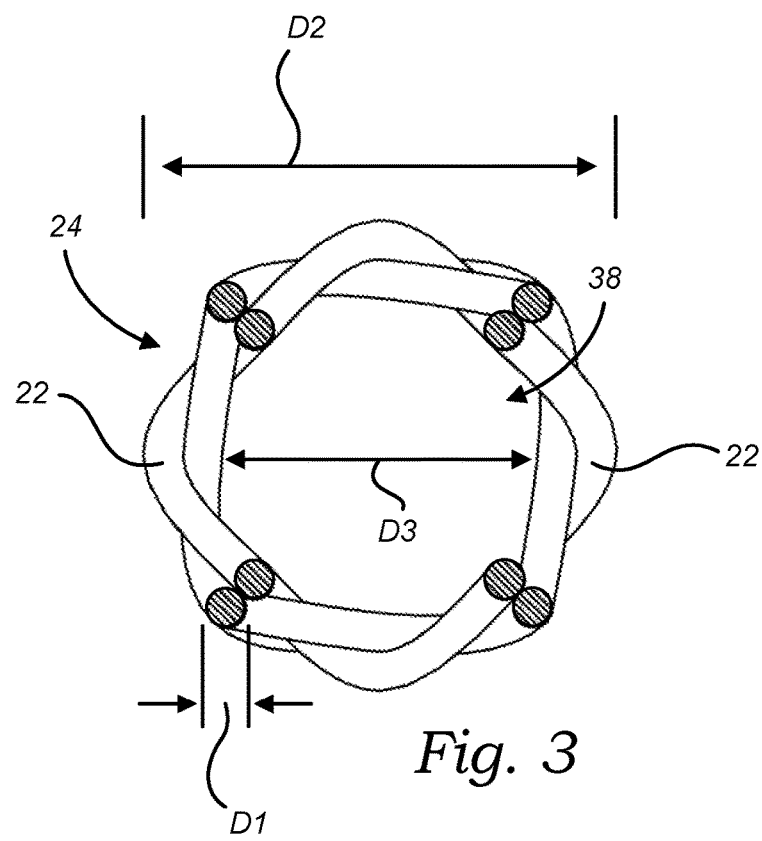
FIG. 3 is a cross-sectional view taken along line 3-3 of FIG. 2.
Figure 4:
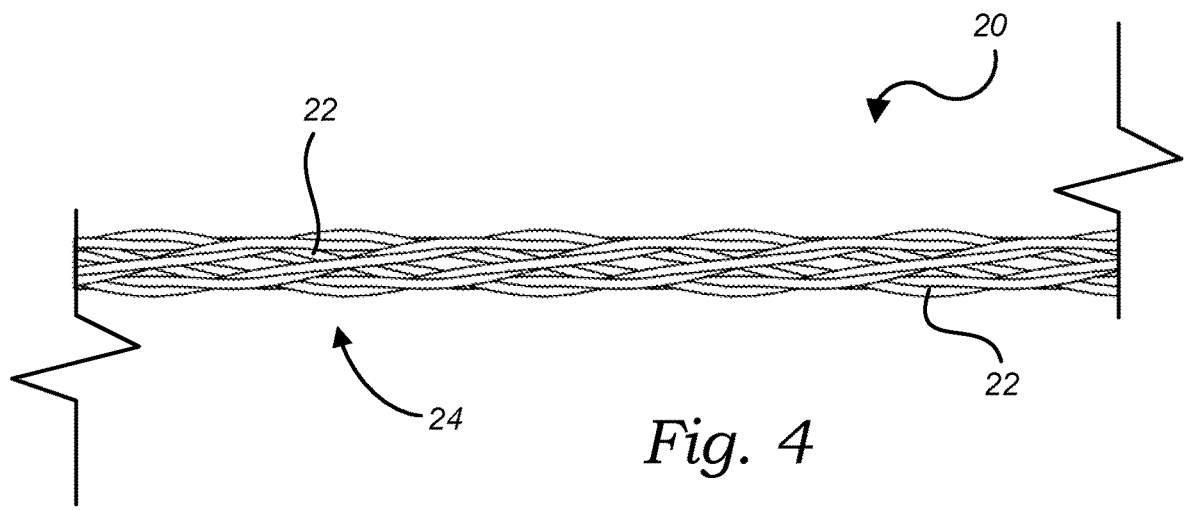
FIG. 4 is a partial side view of a further exemplary braided embolization apparatus, in accordance with at least one embodiment.

FIGS. 2 and 4 illustrate two exemplary braiding patterns that the apparatus 20 may utilize. The embolic braid 24 has a braid density expressed in terms of picks per inch ("PPI"), which represents the number of times the strands 22 cross one another within a given inch of a length L (FIG. 1) of the embolic braid 24. Thus, the more times the strands 22 cross one another (i.e., the greater the PPI value), the greater the braid density. In at least one embodiment, as illustrated in FIG. 2, the embolic braid 24 defines a plurality of braid gaps 36 between strands 22 along the length L of the embolic braid 24. The dimensions and quantity of the braid gaps 36 is dependent upon one or more of the quantity of strands 22 utilized by the embolic braid 24, the strand diameter D1 of each strand 22, and the braid density. Thus, in further embodiments, as illustrated in FIG. 4, the embolic braid 24 is configured for eliminating or at least minimizing the dimensions and quantity of the braid gaps 36. Additionally, in at least one embodiment, as illustrated in FIG. 2, the strands 22 are arranged in a relatively lower density braid pattern that forms an open, substantially tubular central core 38 extending between the proximal and distal ends 26 and 32 and defining an inner diameter D3 within the embolic braid 24, as illustrated in the cross-sectional view of FIG. 3. In at least one alternate embodiment, as illustrated in FIG. 4, the strands 22 are arranged in a relatively higher density braid pattern that minimizes or eliminates the inner diameter D3. It should be noted that the specific braiding patterns illustrated in the accompanying figures are merely exemplary and are being shown and described for illustrative purposes only. In still further embodiments, the strands 22 of the embolic braid 24 may be braided using any braid, knit, or weave patterns now known or later developed (the terms "braid" and "braided" as used herein intended to be all-encompassing for simplicity purposes)—including but in no way limited to 1-over-1-under-1, 1-over-2-under-2, 2-over-2-under-2, etc.—so long as the apparatus 20 is able to substantially carry out the functionality described herein. Similarly, the braid densities and braid gaps 36 depicted in the drawings are merely exemplary as well. In still further embodiments, the embolic braid 24 may utilize any other braid densities, and the braid gaps 36 may take on any other sizes, shapes, quantities, dimensions or patterns, now known or later developed, so long as the apparatus 20 is able to substantially carry out the functionality described herein. Similarly, the strands 22 themselves may each take on any other sizes, quantities or dimensions, now known or later developed, so long as the apparatus 20 is able to substantially carry out the functionality described herein. For example, in at least one embodiment, each of the strands 22 may have a round shape, a flat shape, a square shape, a hexagonal shape, an oval shape, a ribbon shape, a hollow/tubular shape, etc. in cross-section.

In at least one embodiment, the embolic braid 24 is comprised of between 2 and 288 individual strands 22, with each strand 22 having a strand diameter D1 of between 0.0002 inches and 0.003 inches, such that the embolic braid 24 has a primary diameter D2 of between 0.0 inches and 0.0270 inches and an inner diameter D3 of between 0.0 inches and 0.0262 inches. Additionally, in at least one embodiment, the embolic braid 24 has a braid density of between 10 PPI and 250 PPI. The below table contains select non-limiting examples of further exemplary embolic braids 24, which are being provided for illustrative purposes only in order to facilitate a more complete understanding of representative embodiments now contemplated. These examples are intended to be a mere subset of all possible embodiments of the apparatus 20. Thus, these examples should not be construed to limit any of the embodiments described in the present specification. In still further embodiments, other embolic braids 24 having other numerical values for one or more of these parameters may be utilized, so long as the apparatus 20 is able to substantially carry out the functionality described herein. Additionally, it should be noted that these embolic braid 24 examples are intended to include any and all possible combinations of the respective numerical values falling within the identified ranges, along with the recited materials.

TABLE I

| No. of Strands | Strand Diameter (inches) | Primary Diameter (inches) | Inner Diameter (inches) | Braid Density (PPI) | Exemplary Strand Materials |
|---|---|---|---|---|---|
| 2 | 0.00075 | 0.012 | 0.00500 | 50 | platinum-iridium, nitinol |
| 4 | 0.00100 | 0.017 | 0.00525 | 70 | cobalt-chromium, platinum-iridium, nitinol |
| 8 | 0.00110 | 0.021 | 0.02100 | 80 | nitinol, platinum-iridium |
| 16 | 0.00170 | 0.027 | 0.00500 | 100 | cobalt-chromium, multi-layer composites |

Figure 5:
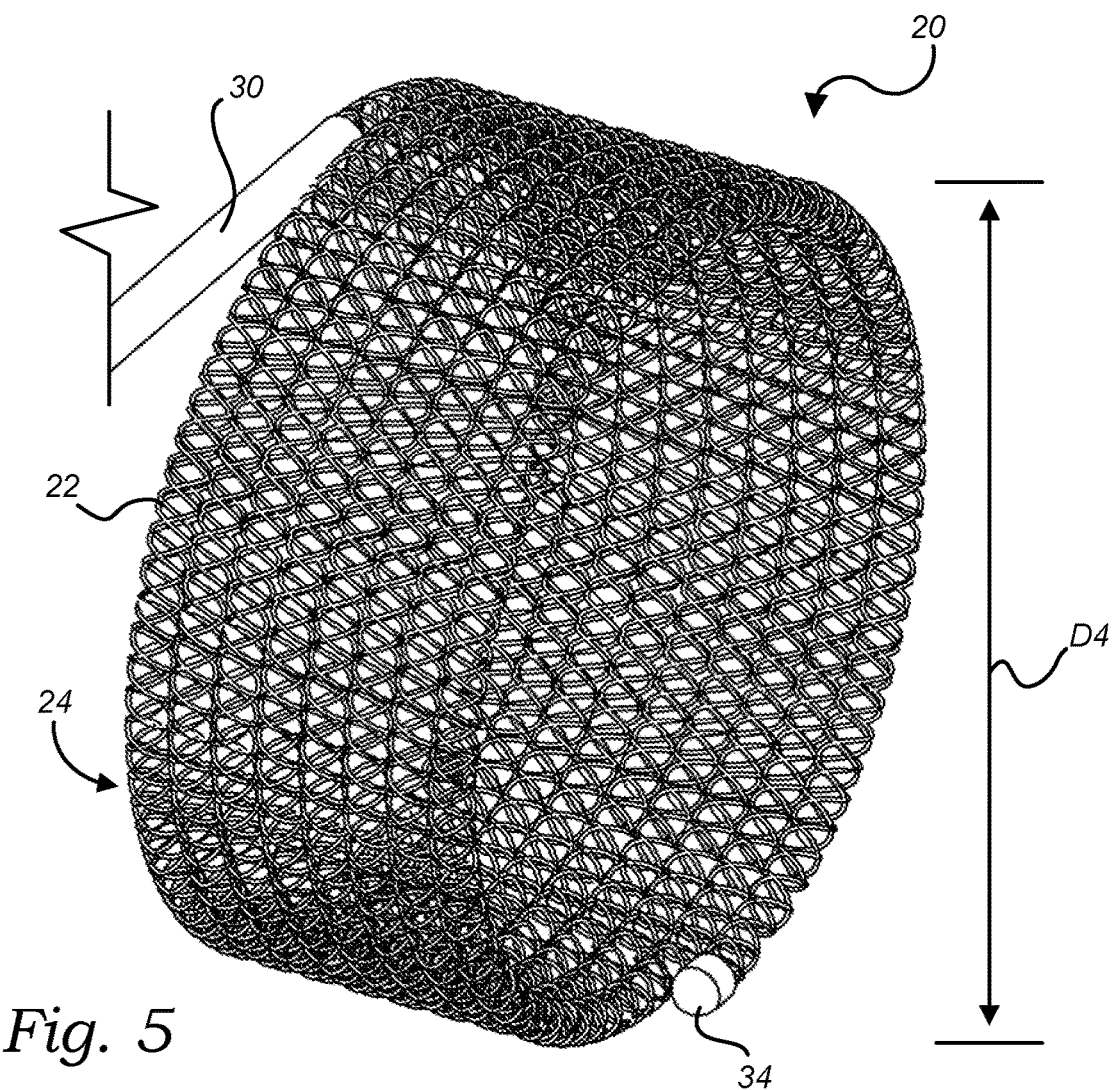
FIG. 5 is a perspective view of the apparatus in a substantially helical secondary shape, in accordance with at least one embodiment.
Figure 6:
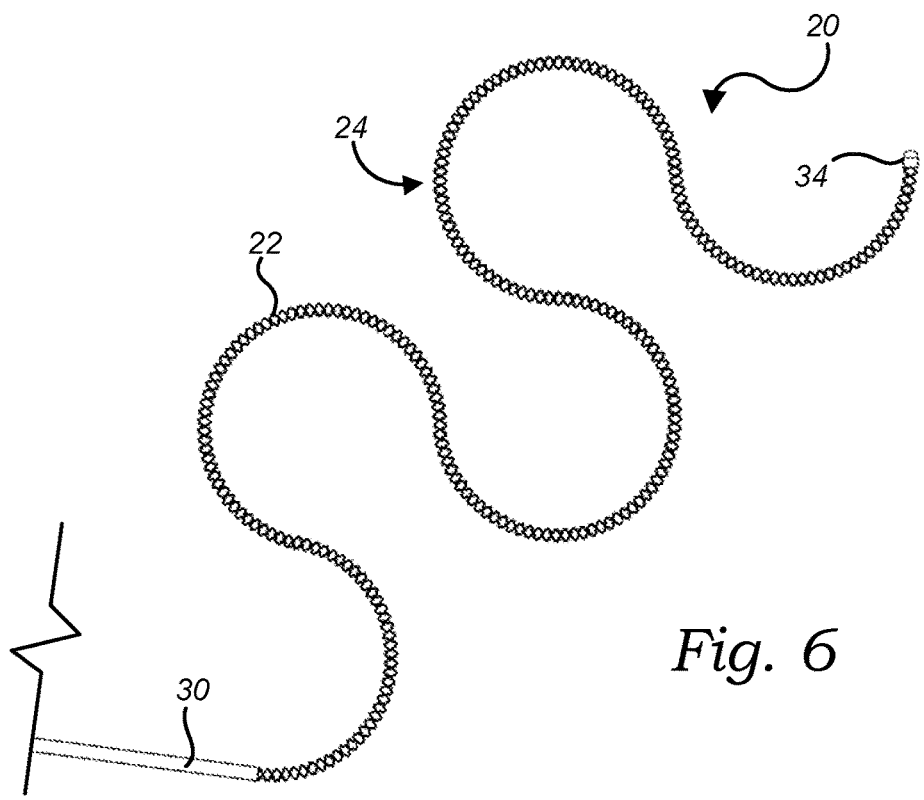
FIG. 6 is a perspective view of the apparatus in a complex spiral secondary shape, in accordance with at least one embodiment.
Figure 7:
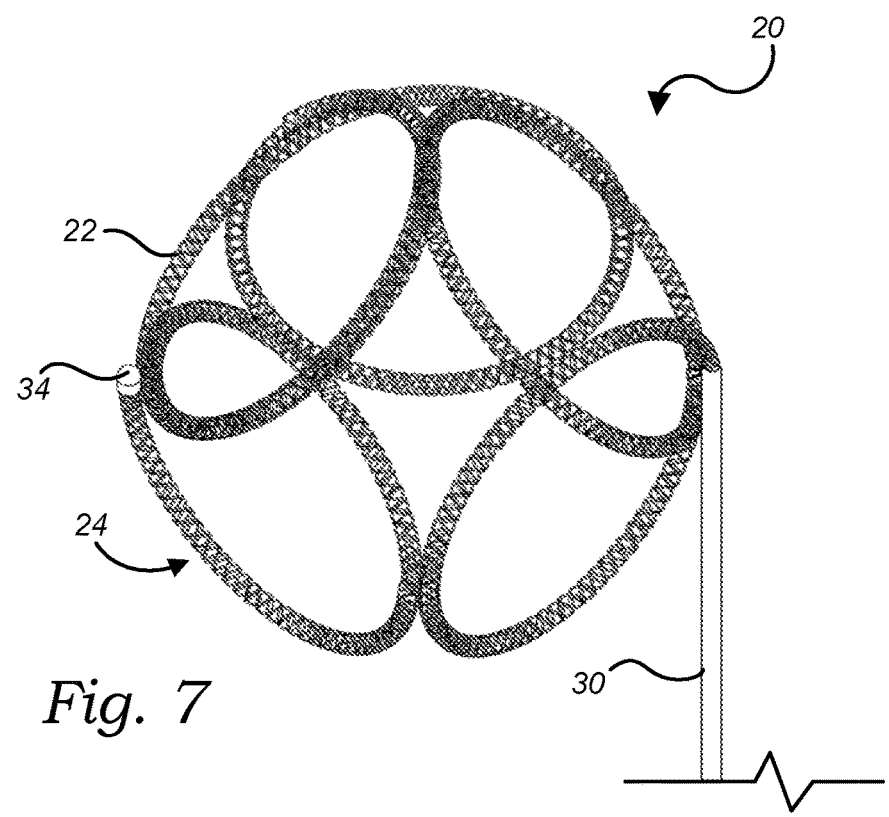
FIG. 7 is a perspective view of the apparatus in a three-dimensional complex secondary shape, in accordance with at least one embodiment.

Referring again to FIG. 1, in at least one embodiment, the elongated primary shape of the embolic braid 24 is suitable for insertion through the catheter 30 into the vascular system with minimal discomfort to the patient. In at least one such embodiment, while in the primary shape, the embolic braid 24 has the shape of an elongated bundle of braided strands 22, as discussed above. Once the embolic braid 24 has reached a target area of the patient's vascular system, it may be deployed to its operative configuration and released from the delivery mechanism 28 so that it will remain in position at the proper location. As illustrated in FIG. 5, once in its operative configuration, the embolic braid 24 takes on a secondary shape. Exemplary secondary shapes of the embolic braid 24 include helices (FIG. 5), vortices, flat spirals, complex spirals (FIG. 6), three-dimensional complex shapes (FIG. 7), spherical, or any other shape—now known or later developed—capable of effectively filling the affected blood vessel, as required by any specific clinical application. Additionally, in at least one embodiment, the secondary shape of the embolic braid 24 may have a variable secondary diameter D4 (i.e., an outer diameter of the embolic braid 24 while in the secondary shape) and/or a variable pitch to fit into and to maintain its position in a specified space within the vascular system. In at least one alternate embodiment, as illustrated in FIG. 5, the secondary shape of the embolic braid 24 may have a uniform secondary diameter D4 and/or a uniform pitch. The specific details of the size and shape of the secondary shape thus can be selected to fit the requirements of the medical procedure for which the apparatus 20 is to be used. Accordingly, the sizes, shapes and dimensions of each of the primary shapes and secondary shapes depicted in the accompanying figures are merely exemplary and shown for illustrative purposes. Additionally, any appropriate methods or techniques for setting the secondary shape of the embolic braid 24, now known or later developed, may be utilized, such as use of high heat or memory shape material, for example.

In at least one embodiment, given that the strands 22 of the embolic braid 24 are braided together and joined both distally via the end cap 34 and proximally via the delivery mechanism 28, the embolic braid 24 is capable of avoiding stretch-related issues that are commonly suffered by traditional embolic coils. In other words, during use of the apparatus 20, should the embolic braid 24 be inserted into the blood vessel of a patient via the catheter 30 and then subsequently be retracted a distance back into the catheter 30, the braided configuration of the embolic braid 24 substantially prevents the embolic braid 24 from stretching, unraveling or otherwise losing its shape—all without the need for stretch-resistant filaments or similar mechanisms. This, in turn, minimizes damage to the blood vessel while also preserving the structural integrity of the embolic braid 24 for continued use. Additionally, the braided nature of the embolic braid 24 creates a relatively larger surface area (compared to traditional embolic coils) that is in contact with the flow of blood, and thus makes the apparatus 20 more efficient at slowing the flow of blood therethrough. This, in turn, enhances the formation of clots that will further preclude blood flow through the region where the apparatus 20 is deployed, such as within an aneurysm for example. Furthermore, because the sizes, shapes, dimensions and relative rigidity of each of the embolic braid 24, primary shape and secondary shape may be selectively tailored (as discussed above), the apparatus 20 is capable of being used as a framing coil, a filling coil, or a packing coil in order to fit the requirements of the medical procedure for which the apparatus 20 is to be used.

Aspects of the present specification may also be described as the following embodiments:

1. A braided embolization apparatus comprising: a plurality of individual strands braided together as an embolic braid having a proximal end and an opposing distal end, the embolic braid forming an elongated primary shape capable of being inserted into a catheter; whereby, during use of the apparatus, upon the distal end the embolic braid subsequently exiting the catheter, the embolic braid is configured for moving into a shape memorized secondary shape capable of filling a target area of a patient's vascular system.

2. The braided embolization apparatus according to embodiment 1, wherein a proximal end of the embolic braid is removably engageable with a delivery mechanism.

3. The braided embolization apparatus according to embodiments 1-2, wherein a distal end of the embolic braid provides an end cap for maintaining the braided arrangement of the strands.

4. The braided embolization apparatus according to embodiments 1-3, wherein the end cap is constructed out of one or more radiopaque materials to facilitate positioning of the embolic braid at a desired location within a blood vessel of a patient.

5. The braided embolization apparatus according to embodiments 1-4, wherein at least one of the strands is comprised of an at least one material that is different from the other strands.

6. The braided embolization apparatus according to embodiments 1-5, wherein at least one of the strands is comprised of an at least one radiopaque material.

7. The braided embolization apparatus according to embodiments 1-6, wherein at least one of the strands is comprised of an at least one non-radiopaque material.

8. The braided embolization apparatus according to embodiments 1-7, wherein at least one of the strands is comprised of both radiopaque and non-radiopaque materials.

9. The braided embolization apparatus according to embodiments 1-8, wherein at least one of the strands is impregnated or coated with an at least one therapeutic.

10. The braided embolization apparatus according to embodiments 1-9, wherein the at least one therapeutic promotes thrombosis.

11. The braided embolization apparatus according to embodiments 1-10, wherein the embolic braid defines a plurality of braid gaps between strands along a length of the embolic braid.

12. The braided embolization apparatus according to embodiments 1-11, wherein the embolic braid defines an open, substantially tubular central core extending between the proximal end and distal end of the embolic braid.

13. The braided embolization apparatus according to embodiments 1-12, wherein the central core defines an inner diameter of between 0.0 inches and 0.0262 inches.

14. The braided embolization apparatus according to embodiments 1-13, wherein the strands are braided together using at least one of a 1-over-1-under-1 pattern, a 1-over-2-under-2 pattern, and a 2-over-2-under-2 pattern.

15. The braided embolization apparatus according to embodiments 1-14, wherein the embolic braid comprises between 2 and 288 individual strands braided together.

16. The braided embolization apparatus according to embodiments 1-15, wherein each of the strands has a strand diameter of between 0.0002 inches and 0.003 inches.

17. The braided embolization apparatus according to embodiments 1-16, wherein at least one of the strands has a strand diameter that is different from the strand diameter of the other strands.

18. The braided embolization apparatus according to embodiments 1-17, wherein the embolic braid has a primary diameter of between 0.0 inches and 0.0270 inches.

19. The braided embolization apparatus according to embodiments 1-18, wherein the embolic braid has a braid density of between 10 PPI and 250 PPI.

20. The braided embolization apparatus according to embodiments 1-19, wherein the secondary shape is at least one of a helical shape, a vortical shape, a flat spiral shape, a complex spiral shape, and a three-dimensional shape.

21. A braided embolization apparatus comprising: a plurality of individual strands braided together as an embolic braid having a proximal end and an opposing distal end, the embolic braid forming an elongated primary shape capable of being inserted into a catheter; and an end cap engaged with the distal end for maintaining the braided arrangement of the strands; whereby, during use of the apparatus, upon the distal end the embolic braid subsequently exiting the catheter, the embolic braid is configured for moving into a shape memorized secondary shape capable of filling a target area of a patient's vascular system.

22. A braided embolization apparatus comprising: a plurality of individual strands braided together as an embolic braid having an elongated primary shape capable of being inserted into a catheter; a proximal end of the embolic braid removably engageable with a delivery mechanism; and an opposing distal end of the embolic braid providing an end cap for maintaining the braided arrangement of the strands; whereby, during use of the apparatus, upon the distal end the embolic braid subsequently exiting the catheter, the embolic braid is configured for moving into a shape memorized secondary shape capable of filling a target area of a patient's vascular system.

In closing, regarding the exemplary embodiments of the present invention as shown and described herein, it will be appreciated that a braided embolization apparatus is disclosed and configured for providing improved stretch resistance, maximized surface area, increased radiopacity and improved shape retention, thereby resulting in a more effective treatment of cerebral aneurysms and cerebral arteriovenous malformations. Because the principles of the invention may be practiced in a number of configurations beyond those shown and described, it is to be understood that the invention is not in any way limited by the exemplary embodiments, but is generally directed to a braided embolization apparatus and is able to take numerous forms to do so without departing from the spirit and scope of the invention. It will also be appreciated by those skilled in the art that the present invention is not limited to the particular geometries and materials of construction disclosed, but may instead entail other functionally comparable structures or materials, now known or later developed, without departing from the spirit and scope of the invention.

Certain embodiments of the present invention are described herein, including the best mode known to the inventor(s) for carrying out the invention. Of course, variations on these described embodiments will become apparent to those of ordinary skill in the art upon reading the foregoing description. The inventor(s) expect skilled artisans to employ such variations as appropriate, and the inventor(s) intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein. Similarly, as used herein, unless indicated to the contrary, the term "substantially" is a term of degree intended to indicate an approximation of the characteristic, item, quantity, parameter, property, or term so qualified, encompassing a range that can be understood and construed by those of ordinary skill in the art.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (along with equivalent open-ended transitional phrases thereof such as "including," "containing" and "having") encompasses all the expressly recited elements, limitations, steps and/or features alone or in combination with un-recited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amendment for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim, whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (along with equivalent open-ended transitional phrases thereof) includes within its meaning, as a limiting case, claimed subject matter specified by the closed-ended transitional phrases "consisting of" or "consisting essentially of." As such, embodiments described herein or so claimed with the phrase "comprising" are expressly or inherently unambiguously described, enabled and supported herein for the phrases "consisting essentially of" and "consisting of."

Any claims intended to be treated under 35 U.S.C. § 112(f) will begin with the words "means for," but use of the term "for" in any other context is not intended to invoke treatment under 35 U.S.C. § 112(f). Accordingly, Applicant reserves the right to pursue additional claims after filing this application, in either this application or in a continuing application.

It should be understood that the methods, and the order in which the respective elements of each method are performed are purely exemplary. Depending on the implementation, they may be performed in any order or in parallel, unless indicated otherwise in the present disclosure.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

While aspects of the invention have been described with reference to at least one exemplary embodiment, it is to be clearly understood by those skilled in the art that the invention is not limited thereto. Rather, the scope of the invention is to be interpreted only in conjunction with the appended claims and it is made clear, here, that the inventor(s) believe that the claimed subject matter is the invention.

What is claimed is:

1. A braided embolization apparatus comprising:
   a plurality of individual strands braided together as an embolic braid having a proximal end and an opposing distal end, the embolic braid forming an elongated primary shape having no inner diameter along substantially an entire length thereof between the proximal and distal ends so as to be capable of being inserted into a catheter, the strands being joined with one another or otherwise finished at each of the proximal and distal ends so as to maintain the braided arrangement of the strands;
   whereby, during use of the apparatus, the embolic braid is configured for moving into a shape memorized secondary shape capable of filling a target area of a patient's vascular system as the embolic braid exits the catheter, and upon the embolic braid subsequently being retracted a distance back into the catheter, the embolic braid is configured for substantially returning to the primary shape without stretching or unraveling of the braided strands.

2. The braided embolization apparatus of claim 1, wherein a proximal end of the embolic braid is removably engageable with a delivery mechanism.

3. The braided embolization apparatus of claim 1, wherein a distal end of the embolic braid provides an end cap for maintaining the braided arrangement of the strands.

4. The braided embolization apparatus of claim 3, wherein the end cap is constructed out of one or more radiopaque materials to facilitate positioning of the embolic braid at a desired location within a blood vessel of a patient.

5. The braided embolization apparatus of claim 1, wherein at least one of the strands is comprised of an at least one material that is different from the other strands.

6. The braided embolization apparatus of claim 5, wherein at least one of the strands is comprised of an at least one radiopaque material.

7. The braided embolization apparatus of claim 5, wherein at least one of the strands is comprised of an at least one non-radiopaque material.

8. The braided embolization apparatus of claim 5, wherein at least one of the strands is comprised of both radiopaque and non-radiopaque materials.

9. The braided embolization apparatus of claim 1, wherein at least one of the strands is impregnated or coated with an at least one therapeutic.

10. The braided embolization apparatus of claim 1, wherein the embolic braid defines a plurality of braid gaps between strands along a length of the embolic braid.

11. The braided embolization apparatus of claim 1, wherein the embolic braid comprises between 2 and 288 individual strands braided together.

12. The braided embolization apparatus of claim 1, wherein each of the strands has a strand diameter of between 0.0002 inches and 0.003 inches.

13. The braided embolization apparatus of claim 12, wherein at least one of the strands has a strand diameter that is different from the strand diameter of the other strands.

14. The braided embolization apparatus of claim 1, wherein the embolic braid has a primary diameter of between 0.0 inches and 0.0270 inches.

15. The braided embolization apparatus of claim 1, wherein the embolic braid has a braid density of between 10 PPI and 250 PPI.

16. The braided embolization apparatus of claim 1, wherein the secondary shape is at least one of a helical shape, a vortical shape, a flat spiral shape, a complex spiral shape, and a three-dimensional shape.

17. A braided embolization apparatus comprising:
   a plurality of individual strands braided together as an embolic braid having a proximal end and an opposing distal end, the embolic braid forming an elongated primary shape having no inner diameter along substantially an entire length thereof between the proximal and distal ends so as to be capable of being inserted into a catheter, the strands being joined with one another or otherwise finished at each of the proximal and distal ends so as to maintain the braided arrangement of the strands; and
   the distal end of the embolic braid providing an end cap;
   whereby, during use of the apparatus, the embolic braid is configured for moving into a shape memorized secondary shape capable of filling a target area of a patient's vascular system as the embolic braid exits the catheter, and upon the embolic braid subsequently being retracted a distance back into the catheter, the embolic braid is configured for substantially returning to the primary shape without stretching or unraveling of the braided strands.

18. A braided embolization apparatus comprising:
   a plurality of individual strands braided together as an embolic braid having a proximal end and an opposing distal end, the embolic braid forming an elongated primary shape having no inner diameter along substantially an entire length thereof between the proximal and distal ends so as to be capable of being inserted into a catheter, the strands being joined with one another or otherwise finished at each of the proximal and distal ends so as to maintain the braided arrangement of the strands;

the proximal end of the embolic braid removably engageable with a delivery mechanism; and the distal end of the embolic braid providing an end cap;

whereby, during use of the apparatus, the embolic braid is configured for moving into a shape memorized secondary shape capable of filling a target area of a patient's vascular system as the embolic braid exits the catheter, and upon the embolic braid subsequently being retracted a distance back into the catheter, the embolic braid is configured for substantially returning to the primary shape without stretching or unraveling of the braided strands.

\* \* \* \* \*